US008946468B2

(12) United States Patent
Kaneda et al.

(10) Patent No.: US 8,946,468 B2
(45) Date of Patent: Feb. 3, 2015

(54) PROCESS FOR PRODUCING ESTER COMPOUND HAVING AN INTERNAL UNSATURATED BOND OR CYCLIC OLEFIN

(75) Inventors: Kiyotomi Kaneda, Suita (JP); Hisashi Sone, Tokyo (JP)

(73) Assignees: JX Nippon Oil & Energy Corporation, Tokyo (JP); Osaka University, Osaka (JP)

( * ) Notice: Subject to any disclaimer, the term of this patent is extended or adjusted under 35 U.S.C. 154(b) by 170 days.

(21) Appl. No.: 13/579,396

(22) PCT Filed: Feb. 18, 2011

(86) PCT No.: PCT/JP2011/053560
§ 371 (c)(1),
(2), (4) Date: Aug. 16, 2012

(87) PCT Pub. No.: WO2011/102484
PCT Pub. Date: Aug. 25, 2011

(65) Prior Publication Data
US 2012/0316360 A1  Dec. 13, 2012

(30) Foreign Application Priority Data

Feb. 19, 2010  (JP) ................................. 2010-034754

(51) Int. Cl.
*C07C 67/055*  (2006.01)
(52) U.S. Cl.
CPC ........... *C07C 67/055* (2013.01); *C07C 2101/16* (2013.01)
USPC ....................................................... 560/243
(58) Field of Classification Search
CPC .................................................. C07C 67/055
See application file for complete search history.

(56) References Cited

PUBLICATIONS

Hansson et al, Journal of Organic Chemistry, Preparation of Allylic Acetates from Simple Alkenes by Palladium (II)-Catalyzed Acetoxylation, 1990, 55, pp. 975-984.*

Jia et al, Journal of Molecular Catalysis A: Chemical, Palladium-catalyzed Allylic Acetoxylation of Olefins Using Hydrogen Peroxide as Oxidant, 1995, 101, pp. 127-136.*
International Preliminary Examination Report dated Sep. 27, 2012 (mailed), corresponding with International Application PCT/JP2011/053560.
International Search Report dated May 24, 2011, corresponding with International Application PCT/JP2011/053560.
Jiro Tsuji et al., "A Novel Synthetic Method for y-Acetoxy-(E)-a,B-Unsaturated Esters by the Palladium Catalyzed Regio- and Stereoselective Acetoxylation of B,y-Unsaturated Esters", Tetrahedron Letters, vol. 22, 1981, pp. 131-134.
Takato Mitsudome et al., "Convenient and Efficient Pd-Catalyzed Regioselective Oxyfunctionalization of Terminal Olefins by Using Molecular Oxygen as Sole Reoxidant", Angew. Chem., vol. 45, 2006, pp. 481-485.
Jan E. Backvall et al., "Dual Stereoseclectivity in the Nucleophilic Attack on (n-Allyl) palladium Complexes", J. Am. Chem. Soc., vol. 107, 1985, pp. 6892-6898.
Kenji Kobata et al., "Capsaicinol: Synthesis by Allylic Oxidation and its Effect on TRPVI-Expressing Cells and Adrenaline Secretion in Rats", Biosci. Biotechnol. Biochem., vol. 70, No. 8, 2006, pp. 1904-1912.
J.E. Backvall et al., "Stereocontrolled Synthesis of (R*R*)-and (R*S*)-5-Hydroxy-2-Methylhexanoic acid Lactones", Tetrahedron, vol. 41, No. 24, 1985, pp. 5761-5764.
Heumann et al., "Allylic Acetoxylation of Cycloalkenes: 2-Cyclohepten-1-yl Acetate", Organic Syntheses, vol. 68, 1990, pp. 109-115.
Mark Chen et al., "A Sulfoxide-Promoted, Catalytic Method for the Regioselective Synthesis of Allylic Acetates from Monosubstituted Olefins via C-H Oxidation", J. Am. Chem. Soc., vol. 126, pp. 1346-1347, 2004.
Mark Chen et al., "Serial Ligand Catalysis: A Highly Selective Allylic C-H Oxidation", J. Am. Chem. Soc., vol. 127, 2005, pp. 6970-6971.

* cited by examiner

*Primary Examiner* — Paul A Zucker
(74) *Attorney, Agent, or Firm* — Fitch, Even, Tabin & Flannery LLP

(57) ABSTRACT

A process for producing an unsaturated bond-containing ester compound includes reacting an internal olefin or a cyclic olefin having one carbon-carbon double bond or more at a position other than terminals of a molecule thereof (the internal olefin and the cyclic olefin may each contain a hetero atom) with a carboxylic acid in an amide-based solvent represented by a formula (1) in the presence of a palladium catalyst, a base, and molecular oxygen, to obtain an ester compound having an unsaturated bond.

7 Claims, No Drawings

PROCESS FOR PRODUCING ESTER COMPOUND HAVING AN INTERNAL UNSATURATED BOND OR CYCLIC OLEFIN

CROSS-REFERENCE TO RELATED APPLICATIONS

This Application is a U.S. National Stage Application filed under 35 U.S.C. §371 of International Application PCT/JP2011/053560, filed Feb. 18, 2011, designating the United States, which claims priority from Japanese Patent Application 2010-034754, filed Feb. 19, 2010, the complete disclosures of which are hereby incorporated herein by reference in their entirety for all purposes.

TECHNICAL FIELD

The present invention relates to a process for producing an ester compound having an α,β-unsaturated bond by esterifying an olefin through oxidative bonding of a carboxyl group.

BACKGROUND ART

Diols such as 1,3-butanediol and 1,4-butanediol and esters such as butyl acetate and propyl acetate are industrially useful as solvents and raw material chemicals, and have been used in various fields as plastic raw materials, cosmetics, flavors, fragrances, and the like.

Such a diol has been manufactured by reaction of an alkyne such as acetylene with an aldehyde followed by hydrogenation of the product, or by diacetoxylation of a diene compound such as butadiene followed by reduction and hydrolysis. However, acetylene has problems in terms of safety and stable availability.

Meanwhile, as a method for manufacturing an ester, a method is known in which a carboxylic acid and an alcohol are reacted with each other in the presence of an acid catalyst. Moreover, J. Am. Chem. Soc., 2005, vol. 127, p. 6970 to 6971 (NPL 1) and J. Am. Chem. Soc., 2004, vol. 126, p. 1346 to 1347 (NPL 2) disclose that ester compounds having an α,β-unsaturated bond can be obtained by reactions of acetic acid with various terminal olefins in a sulfoxide solvent such as dimethyl sulfoxide in the presence of a palladium catalyst and an oxidizing agent such as benzoquinone.

Terminal olefins can be esterified by the method described in NPL 1 or 2. However, since internal olefins and cyclic olefins have low reactivities, it is difficult to obtain by these methods ester compounds having an α,β-unsaturated bond at relatively high yields by using these olefins as raw materials. In addition, when a mixture olefin containing not only a terminal olefin, but also an internal olefin or a cyclic olefin is used as a raw material, there is a problem that only the terminal olefin is esterified, and the internal olefin or the cyclic olefin remains unreacted.

Meanwhile, Angew. Chem. Int. Ed., 2006, vol. 45, p. 481 to 485 (NPL 3) discloses that ester compounds having an α,β-unsaturated bond can be obtained by reactions of acetic acid with various terminal olefins in N,N-dimethylacetamide in the presence of a palladium catalyst and sodium acetate.

CITATION LIST

Non Patent Literature

[NPL 1] M. S. Chen et al., J. Am. Chem. Soc., 2005, vol. 127, p. 6970 to 6971

[NPL 2] M. S. Chen et al., J. Am. Chem. Soc., 2004, vol. 126, p. 1346 to 1347

[NPL 3] T. Mitsudome et al., Angew. Chem. Int. Ed., 2006, vol. 45, p. 481 to 485

SUMMARY OF INVENTION

Technical Problem

The present invention has been made in view of the above-described problems of the conventional techniques. An object of the present invention is to provide a process capable of producing an ester compound having an α,β-unsaturated bond from an internal olefin or a cyclic olefin at a relatively high yield.

Solution to Problem

The present inventors have conducted earnest study to achieve the above object. As a result, the present inventors found the following fact. Specifically, use of a specific amide-based solvent in the presence of a palladium catalyst, a base, and molecular oxygen makes it possible to react a carboxylic acid with an internal olefin or a cyclic olefin having one carbon-carbon double bond or more at a position other than terminals of a molecule thereof. As a result, the internal olefin or the cyclic olefin is oxidatively esterified (specifically, esterified through oxidative bonding of a carboxyl group), so that an ester compound having an α,β-unsaturated bond, which is difficult to manufacture from the internal olefin or the cyclic olefin by the conventional methods, can be manufactured therefrom at a relatively high yield. This finding has led to the completion of the present invention.

Specifically, a process for producing an α,β-unsaturated bond-containing ester compound of the present invention comprises:

reacting an internal olefin or a cyclic olefin having one carbon-carbon double bond or more at a position other than terminals of a molecule thereof (the internal olefin and the cyclic olefin may each contain a hetero atom) with a carboxylic acid in an amide-based solvent in the presence of a palladium catalyst, a base, and molecular oxygen, thereby bonding a carboxyl group of the carboxylic acid to at least one of carbon atoms constituting the carbon-carbon double bond and carbon atoms at allylic positions of the internal olefin or the cyclic olefin, to obtain an ester compound having an α,β-unsaturated bond, the amide-based solvent being represented by the following formula (1):

[Chem. 1]

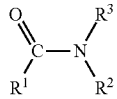

(1)

(in the formula (1), $R^1$ represents an alkyl group having 1 to 4 carbon atoms; $R^2$ and $R^3$ each independently represent an alkyl group having 1 to 4 carbon atoms or an aryl group; and when $R^1$ and $R^2$ are alkyl groups, $R^1$ and $R^2$ may be bonded to each other to form a ring structure).

In the process for producing an α,β-unsaturated bond-containing ester compound of the present invention, the internal olefin or the cyclic olefin is preferably a compound represented by the following formula (2):

[Chem. 2]

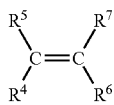
(2)

(in the formula (2), $R^4$ to $R^7$ each independently represent one selected from the group consisting of a hydrogen atom, alkyl groups, alkenyl groups, and aryl groups; the alkyl group, the alkenyl group, and the aryl group may each contain a hetero atom; at least one of $R^4$ and $R^5$ is any one of alkyl groups, alkenyl groups, and aryl groups; at least one of $R^6$ and $R^7$ is any one of alkyl groups, alkenyl groups, and aryl groups; when $R^4$ and $R^6$ are each an alkyl group or an alkenyl group, $R^4$ and $R^6$ may be bonded to each other to form a ring structure; and when $R^5$ and $R^7$ are each an alkyl group or an alkenyl group, $R^5$ and $R^7$ may be bonded to each other to form a ring structure). The internal olefin or the cyclic olefin more preferably does not have any carbon-carbon double bond at the terminals of the molecule thereof.

In addition, the α,β-unsaturated bond-containing ester compound obtained by the process of the present invention is preferably a compound represented by the following formula (3):

[Chem. 3]

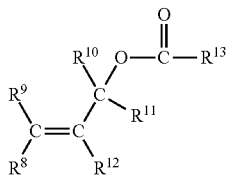
(3)

(in the formula (3), $R^8$ to $R^{13}$ each independently represent one selected from the group consisting of a hydrogen atom, alkyl groups, alkenyl groups, and aryl groups; the alkyl group, the alkenyl group, and the aryl group may each contain a hetero atom; at least one of $R^8$ to $R^{11}$ is any one of alkyl groups, alkenyl groups, and aryl groups; when $R^8$ and $R^{12}$ are each an alkyl group or an alkenyl group, $R^8$ and $R^{12}$ may be bonded to each other to form a ring structure; and when $R^9$ and $R^{10}$ or $R^{11}$ are each an alkyl group or an alkenyl group, $R^9$ and $R^{10}$ or $R^{11}$ may be bonded to each other to form a ring structure).

In the process for producing an α,β-unsaturated bond-containing ester compound of the present invention, a concentration of the palladium catalyst is preferably 0.002 to 1 mol/L, and the palladium catalyst is preferably a palladium halide. The amide-based solvent is preferably N,N-dimethylacetamide.

In the process for producing an α,β-unsaturated bond-containing ester compound of the present invention, the internal olefin or the cyclic olefin is preferably reacted with the carboxylic acid in the absence of any copper catalyst. In addition, acetic acid is preferably used as the carboxylic acid. In this case, an acetoxyl group is bonded to a carbon atom at an allylic position of an obtained ester compound having an α,β-unsaturated bond.

Moreover, a diester compound having an α,β-unsaturated bond can be manufactured by reacting an α,β-unsaturated bond-containing monoester compound obtained by the process for producing an α,β-unsaturated bond-containing ester compound of the present invention with a carboxylic acid in an amide-based solvent represented by the above-described formula (1) in the presence of a palladium catalyst, a base, and molecular oxygen, thereby bonding a carboxyl group of the carboxylic acid to at least one of carbon atoms constituting a carbon-carbon double bond in the α,β-unsaturated bond-containing monoester compound and carbon atoms at allylic positions of the α,β-unsaturated bond-containing monoester compound.

Note that although it is not exactly clear why the reaction of an internal olefin or a cyclic olefin with a carboxylic acid by the production process of the present invention makes it possible to manufacture an ester compound having an α,β-unsaturated bond (hereinafter, referred to as an "α,β-unsaturated bond-containing ester compound") at a relatively high yield, the present inventors speculate as follows. Specifically, an internal olefin or a cyclic olefin has a lower reactivity than a terminal olefin. Hence, if a carboxylic acid is attempted to react with an internal olefin or a cyclic olefin, the esterification reaction through oxidative bonding of a carboxyl group proceeds insufficiently by conventional methods using a palladium catalyst. Moreover, since isomerization reaction of the olefin occurs, the amount of the α,β-unsaturated bond-containing ester produced decreases. Presumably because of these reasons, the yield of the α,β-unsaturated bond-containing ester compound is lowered.

On the other hand, it is possible to use only molecular oxygen as the reoxidizing agent without copper in the process for producing an α,β-unsaturated bond-containing ester compound of the present invention. Hence, the esterification reaction can be caused to proceed efficiently in which a carboxyl group is also oxidatively bonded to an internal olefin or a cyclic olefin, which has a lower reactivity than a terminal olefin. Moreover, isomerization reaction of the olefin does not occur. Presumably because of these reasons, the yield of the α,β-unsaturated bond-containing ester compound is relatively high.

In addition, although it is not exactly clear why the carboxyl group of the carboxylic acid is bonded to a carbon atom at an allylic position in the process for producing an α,β-unsaturated bond-containing ester compound of the present invention, the present inventors speculates as follows. Specifically, when an internal olefin or a cyclic olefin is mixed with a palladium catalyst, the palladium catalyst coordinates to carbon atoms constituting a carbon-carbon double bond of the internal olefin or the cyclic olefin. At this time, the palladium catalyst presumably coordinates widely to a carbon atom at an allylic position adjacent to the carbon-carbon double bond. Presumably as a result, the carboxylic acid more readily reacts with not only the carbon atoms constituting the carbon-carbon double bond, but also the carbon atom at the allylic position, so that the carboxyl group of the carboxylic acid is bonded also to the carbon atom at the allylic position.

Advantageous Effects of Invention

According to the present invention, it is possible to manufacture an α,β-unsaturated bond-containing ester compound at a relatively high yield by an esterification reaction of an internal olefin or a cyclic olefin with a carboxylic acid through oxidative bonding of a carboxyl group.

DESCRIPTION OF EMBODIMENTS

Hereinafter, the present invention will be described in detail based on preferred embodiments thereof. A process for producing an α,β-unsaturated bond-containing ester compound of the present invention comprises:

reacting an internal olefin or a cyclic olefin having one carbon-carbon double bond or more at a position other than terminals of a molecule thereof with a carboxylic acid in an amide-based solvent in the presence of a palladium catalyst, a base, and molecular oxygen, thereby bonding a carboxyl group of the carboxylic acid to at least one of carbon atoms constituting the carbon-carbon double bond and carbon atoms at allylic positions of the internal olefin or the cyclic olefin, the amide-based solvent being represented by the following formula (1):

[Chem. 4]

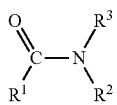

(1)

(in the formula (1), $R^1$ represents an alkyl group having 1 to 4 carbon atoms; $R^2$ and $R^3$ each independently represent an alkyl group having 1 to 4 carbon atoms or an aryl group; and when $R^1$ and $R^2$ are alkyl groups, $R^1$ and $R^2$ may be bonded to each other to form a ring structure).

<Olefin>

The olefin used in the present invention is an internal olefin or a cyclic olefin having one carbon-carbon double bond or more at a position other than terminals of a molecule thereof. In addition, in the present invention, an olefin having or not having a carbon-carbon double bond at a terminal thereof can be used as the internal olefin or the cyclic olefin, as long as the olefin has one carbon-carbon double bond or more at an internal position of the molecule. Moreover, the internal olefin and the cyclic olefin may each contain a hetero atom (preferably an oxygen atom). Examples of the internal olefin and cyclic olefin containing a hetero atom include internal olefins and cyclic olefins having a functional group containing a hetero atom (preferably an oxygen atom), such as an ester group (preferably a carboxylic acid ester group or an alkyl ester group).

The olefin is preferably a compound represented by the following formula (2):

[Chem. 5]

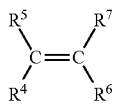

(2)

(in the formula (2), $R^4$ to $R^7$ each independently represent one selected from the group consisting of a hydrogen atom, alkyl groups, alkenyl groups, and aryl groups; at least one of $R^4$ and $R^5$ is any one of alkyl groups, alkenyl groups, and aryl groups; at least one of $R^6$ and $R^7$ is any one of alkyl groups, alkenyl groups, and aryl groups; when $R^4$ and $R^6$ are each an alkyl group or an alkenyl group, $R^4$ and $R^6$ may be bonded to each other to form a ring structure; and when $R^5$ and $R^7$ are each an alkyl group or an alkenyl group, $R^5$ and $R^7$ may be bonded to each other to form a ring structure).

The alkyl group and the alkenyl group may be linear, branched, or cyclic. In addition, the number of carbon atoms of the alkyl group is preferably 1 to 20, and more preferably 4 to 12. Moreover, the alkyl group may contain a hetero atom (preferably an oxygen atom), unless the effect of the present invention is impaired. The position of the C═C bond in the alkenyl group is not particularly limited, and may be at a terminal or internal position of the alkenyl group. For example, an olefin having a C═C bond at a terminal of the alkenyl group is a polyene having C═C bonds at terminal and internal positions of the molecule, and an olefin having a C═C bond at an internal position of the alkenyl group is a polyene having two or more C═C bonds at internal positions of the molecule. Examples of the aryl group include phenyl group, methylphenyl group, benzyl group, and the like. The aryl group may contain a hetero atom (preferably an oxygen atom), unless the effect of the present invention is impaired. Examples of the alkyl group, the alkenyl group, and the aryl group containing a hetero atom include those having a functional group containing a hetero atom (preferably an oxygen atom), such as an ester group (preferably a carboxylic acid ester group (—O—C(═O)—R), or an alkyl ester group (—C(═O)—O—R)).

Moreover, $R^4$ and $R^6$, and/or $R^5$ and $R^7$ may be bonded to each other to form a ring structure. Examples of the ring structure include cyclic olefins such as cycloalkene and cycloalkadiene, and the like. In this case, a C═C bond may be present in a moiety other than the ring structure (for example, in $R^5$ and/or $R^7$, when $R^4$ and $R^6$ are bonded to each other to form the ring structure).

Specific examples of the internal olefin include monoolefins such as 2-butene, 2-pentene, 2-methyl-2-butene, 2-hexene, 3-hexene, 4-methyl-2-pentene, 2-heptene, 3-heptene, 5-methyl-2-hexene, 2-octene, 3-octene, 4-octene, 6-methyl-2-heptene, 2-nonene, 7-methyl-2-octene, 1-phenyl-1-propylene, 1-cyclohexyl-1-propylene, 2-decene, 3-decene, 4-decene, 5-decene, 8-methyl-2-nonene, 1-phenyl-2-butene, 1-cyclohexyl-2-butene, 5-undecene, 6-dodecene, 7-tetradecene, and 8-hexadecene; dienes such as 1,3-pentadiene, 2,4-hexadiene, 2,5-heptadiene, 1,3-octadiene, and 2,4-decadiene; and the like. In addition, isomers such as cis- and trans-isomers of these internal olefins can be used equally.

Specific examples of the cyclic olefin include cycloalkenes such as cyclopentene, cyclohexene, cyclooctene, and cyclodecene; cycloalkadienes typified by cyclooctadiene; cycloalkenes and cycloalkadienes substituted with alkyl groups, alkenyl groups, or the like (for example, vinylcyclohexene and allylcyclohexene); and the like.

In addition, specific examples of the internal olefin containing a hetero atom include acetoxylation products of the above-described monoolefins, such as 2-butene-1-acetate; acetoxylation products of the above-described dienes, such as 1,3-pentadiene-1-acetate; unsaturated carboxylic acid esters, such as methyl oleate; and the like. Isomers such as cis- and trans-isomers of these internal olefins can be used equally. In addition, specific examples of the cyclic olefin containing a hetero atom include acetoxylation products of the above-described cyclic olefins, such as cyclohexene-1-acetate; and the like.

These internal olefins and cyclic olefins may be used singly or in combination of two or more kinds. In addition, of these internal olefins and cyclic olefins, preferred are 2-butene, 2-pentene, 2-methyl-2-butene, 2-hexene, 3-hexene, 4-methyl-2-pentene, 2-heptene, 2-octene, 3-octene, 4-octene, 5-decene, 6-methyl-2-heptene, cyclopentene, cyclohexene, and cyclooctene, more preferred is 2-butene, from the viewpoint that a high yield of the α,β-unsaturated bond-containing ester compound can be achieved.

In the production process of the present invention, a concentration of the internal olefin or the cyclic olefin is preferably 0.01 to 5 mol/L, and more preferably 0.05 to 1 mol/L. If the concentration of the internal olefin or the cyclic olefin is lower than the lower limit, the α,β-unsaturated bond-containing ester compound tends not to be obtained at a high yield. Meanwhile, if the concentration exceeds the upper limit, the α,β-unsaturated bond-containing ester compound tends not to be manufactured at a high yield, because the esterification reaction of the internal olefin or the cyclic olefin through oxidative bonding of a carboxyl group proceeds insufficiently.

<Carboxylic Acid>

The carboxylic acid used in the present invention is not particularly limited, as long as the carboxylic acid has a carboxyl group. From the viewpoint that the target α,β-unsaturated bond-containing ester compound can be obtained at a high yield, saturated aliphatic carboxylic acids such as acetic acid, propionic acid, butyric acid, valeric acid, pivalic acid, caproic acid, octanoic acid, decanoic acid, lauric acid, myristic acid, palmitic acid, and stearic acid; and α,β-unsaturated aliphatic carboxylic acids such as acrylic acid, methacrylic acid, crotonic acid, isocrotonic acid, fumaric acid, and maleic acid are preferable, saturated aliphatic carboxylic acids are more preferable, and acetic acid is particularly preferable. These carboxylic acids may be used singly or in combination of two or more kinds.

In the production process of the present invention, a concentration of the carboxylic acid is preferably 0.01 to 15 mol/L, and more preferably 0.05 to 10 mol/L. If the concentration of the carboxylic acid is lower than the lower limit, the α,β-unsaturated bond-containing ester compound tends not to be obtained at a high yield, because the esterification reaction of the internal olefin or the cyclic olefin thorough oxidative bonding of a carboxyl group proceeds insufficiently. Meanwhile, if the concentration exceeds the upper limit, a problem tends to occur in terms of economic efficiency.

<Palladium Catalyst>

The palladium catalyst used in the present invention is not particularly limited, as long as the palladium catalyst is a compound containing a palladium atom. Specific examples of the palladium catalyst include inorganic salts of palladium such as palladium sulfate, palladium nitrate, and palladium carbonate; polyoxoanionic compounds containing palladium such as heteropolyacid palladium salts and isopolyacid palladium salts; palladium halides such as palladium chloride and palladium bromide; palladates such as sodium tetrachloropalladate, sodium tetrabromopalladate, potassium tetrachloropalladate, and potassium tetrabromopalladate; ammine complexes of palladium halides such as tetraamminepalladium dichloride and diamminepalladium tetrachloride; inorganic palladium compounds and complexes such as palladium hydroxide and palladium oxide; organic acid salts of palladium such as palladium acetate and palladium(II) trifluoroacetate; palladium-containing organic compounds such as palladium acetylacetonate and alkylpalladium compounds; nitrile complexes of palladium halides such as diacetonitrile palladium dichloride and dibenzonitrile palladium dichloride; palladium-phosphine complexes typified by tetrakis(triphenylphosphine)palladium; palladium-amine complexes typified by (ethylenediaminetetraacetic acid)palladium; organic palladium compounds and complexes such as tris(dibenzylideneacetone)dipalladium-chloroform adduct and cyclooctadiene palladium dichloride; active metal palladium such as palladium colloid and highly dispersed palladium metal; and the like. In addition, anhydrides and hydrates of these compounds can be each used as the palladium catalyst. These palladium catalysts may be used singly or in combination of two or more kinds.

Of these palladium catalysts, palladium halides and nitrile complexes of palladium halides are preferable, and palladium halides are more preferable, from the viewpoint that a high yield of the α,β-unsaturated bond-containing ester compound can be achieved in the esterification reaction of the internal olefin or the cyclic olefin through oxidative bonding of a carboxyl group.

In the present invention, the palladium catalyst may be in a form of being dissolved in an amide-based solvent to be described later, in a form of being uniformly or non-uniformly dispersed therein, or in a form of a combination thereof. For example, some of the components of the palladium catalyst (for example, the ligand) may be dissolved in the amide-based solvent, and the rest of the components may be uniformly or non-uniformly dispersed.

Moreover, in the present invention, a concentration of the palladium catalyst is preferably 0.002 to 1 mol/L, and more preferably 0.001 to 0.05 mol/L. If the concentration of the palladium catalyst is lower than the lower limit, the α,β-unsaturated bond-containing ester compound tends not to be manufactured at a high yield, because the esterification reaction of the internal olefin or the cyclic olefin through oxidative bonding of a carboxyl group proceeds insufficiently. Meanwhile, if the concentration exceeds the upper limit, the esterification reaction of the internal olefin or the cyclic olefin through oxidative bonding of a carboxyl group tends to proceed insufficiently because of the formation of Pd black, which is an inactive species.

<Amide-Based Solvent>

In the present invention, the amide-based solvent represented by the formula (1) is used as a solvent. The use of such an amide-based solvent makes it possible to efficiently reoxidize the palladium catalyst with molecular oxygen.

In the formula (1), $R^1$ represents an alkyl group having 1 to 4 carbon atoms; and $R^2$ and $R^3$ each independently represent an alkyl group having 1 to 4 carbon atoms or an aryl group. When $R^1$ and $R^2$ are alkyl groups, $R^1$ and $R^2$ may be bonded to each other to form a ring structure. Examples of such a ring structure include the pyrrolidone skeleton, the caprolactam skeleton, and the like.

Specific examples of the amide-based solvent used in the present invention include N,N-dimethylacetamide, N,N-diethylacetamide, N,N-dipropylacetamide, N-methyl-N-ethylacetamide, N-butyl-N-phenylacetamide, N,N-dimethylpropanamide, N,N-diethylpropanamide, N-methyl-N-ethylpropanamide, N-methyl-2-pyrrolidone, N-methyl-2-caprolactam, N-ethyl-2-caprolactam, and the like. These solvents may be used singly or in combination of two or more kinds. In addition, these amide-based solvents may be used in combination with other solvents, in the present invention.

Of these amide-based solvents, N,N-dimethylacetamide and N-methyl-2-pyrrolidone are preferable, and N,N-dimethylacetamide is more preferable, from the viewpoint that a high yield of the α,β-unsaturated bond-containing ester compound can be achieved in the esterification reaction of the internal olefin or the cyclic olefin through oxidative bonding of a carboxyl group.

In the present invention, the amount of the amide-based solvent used is set as appropriate, such that the concentrations of the internal olefin or the cyclic olefin and of the palladium catalyst can be within the above-described ranges.

<Oxygen>

In the present invention, the palladium catalyst having been used for the esterification of the internal olefin or the cyclic olefin through oxidative bonding of a carboxyl group is reoxidized by using molecular oxygen. Since substantially no co-catalyst such as a copper catalyst is used at this time, the esterification reaction of the internal olefin or the cyclic olefin through oxidative bonding of a carboxyl group is not inhibited by a copper catalyst, so that the α,β-unsaturated bond-containing ester compound can be manufactured from the internal olefin or the cyclic olefin at a relatively high yield.

Examples of the source of the above-described molecular oxygen include oxygen gas, oxygen-enriched air, air, mixture gas of a diluent gas with air or oxygen gas, and the like (these are collectively referred to as "oxygen-containing gases"). Examples of the diluent gas include nitrogen gas, helium gas, argon gas, carbon dioxide, and the like. Nitrogen gas is generally used as the diluent gas.

In the present invention, gases other than these oxygen-containing gases and the diluent gases can be used in combination, unless the effect of the present invention is impaired. Moreover, such an oxygen-containing gas may be fed as a mixture with the amide-based solvent or the like, as needed.

In the present invention, the oxygen-containing gas is preferably fed at an oxygen pressure of 0.1 to 1 MPa (more preferably 0.3 to 1 MPa). If the oxygen pressure is lower than the lower limit, the α,β-unsaturated bond-containing ester compound tends not to be manufactured at a high yield because of the formation of Pd black, which is an inactive species. Meanwhile, if the oxygen pressure exceeds the upper limit, some of internal olefins and cyclic olefins tend to result in formation of oxidized by-products (for example, in the case of cyclohexene, 2-cyclohexen-1-one is formed by oxidation at an allylic position).

<Base>

In the present invention, the reaction of the internal olefin or the cyclic olefin with the carboxylic acid is carried out in the presence of a base. This makes it possible to efficiently manufacture the target α,β-unsaturated bond-containing ester compound. As the base, preferred are strong bases such as sodium hydroxide and calcium hydroxide; weak bases such as sodium hydrogen carbonate, sodium carbonate, potassium hydrogen carbonate, and potassium carbonate; and alkali metal salts (for example, sodium salts, potassium salts, and calcium salts) of the above-described saturated aliphatic carboxylic acids or the above-described α,β-unsaturated aliphatic carboxylic acids, and more preferred are alkali metal salts (particularly preferably a sodium salt) of the carboxylic acid to be reacted with the internal olefin or the cyclic olefin.

The concentration of the base is preferably 0.001 to 1.5 mol/L, and more preferably 0.005 to 1 mol/L. If the concentration of the base is lower than the lower limit, the α,β-unsaturated bond-containing ester compound tends not to be obtained at a high yield, because the esterification reaction of the internal olefin or the cyclic olefin thorough oxidative bonding of a carboxyl group proceeds insufficiently. Meanwhile, if the concentration exceeds the upper limit, the α,β-unsaturated bond-containing ester compound tends not to be obtained at a high yield, because the base is not dissolved completely, so that the esterification reaction of the internal olefin or the cyclic olefin thorough oxidative bonding of a carboxyl group proceeds insufficiently.

<Esterification Reaction>

In the process for producing an α,β-unsaturated bond-containing ester compound of the present invention, the internal olefin or the cyclic olefin (the internal olefin and the cyclic olefin may each contain a hetero atom) is reacted with the carboxylic acid in the amide-based solvent in the presence of the palladium catalyst, the base, and the molecular oxygen, thereby bonding a carboxyl group of the carboxylic acid to at least one of carbon atoms constituting the C=C bond in the olefin and carbon atoms at allylic positions of the olefin. Note that a "carbon atom at an allylic position" means a carbon atom adjacent to a C=C bond, in either case where the olefin is an open-chain or cyclic olefin. For example, in the case of 2-butene, a carbon atom at position 1 is a carbon atom at an allylic position. In the case of 3-octene, carbon atoms at positions 2 and 5 are each a carbon atom at an allylic position. In the case of 4-octene, a carbon atom at position 3 is a carbon atom at an allylic position. In the case of cyclohexene, a carbon atom at position 3 is a carbon atom at an allylic position.

In such a reaction, the α,β-unsaturated bond-containing ester compound is formed not only when the carboxyl group of the carboxylic acid is bonded to a carbon atom at an allylic position of the internal olefin or the cyclic olefin, but also when the carboxyl group of the carboxylic acid is bonded to one of the carbon atoms constituting the C=C bond, and the other carbon atom forms a double bond with an adjacent carbon atom other than the carbon atom to which the carboxyl group is bonded.

In addition, when the internal olefin or the cyclic olefin contains a hetero atom, the carboxyl group of the carboxylic acid can be bonded to at least one of carbon atoms constituting the C=C bond in the olefin and carbon atoms at allylic positions of the olefin, without oxidizing a functional group containing the hetero atom.

For example, when the internal olefin or the cyclic olefin represented by the formula (2) is reacted with the carboxylic acid as described above, an α,β-unsaturated bond-containing ester compound represented by the following formula (3) is formed:

[Chem. 6]

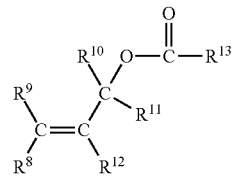

(3)

(in the formula (3), $R^8$ to $R^{13}$ each independently represent one selected from the group consisting of a hydrogen atom, alkyl groups, alkenyl groups, and aryl groups, at least one of $R^8$ to $R^{11}$ is any one of alkyl groups, alkenyl groups, and aryl groups; when $R^8$ and $R^{12}$ are each an alkyl group or an alkenyl group, $R^8$ and $R^{12}$ may be bonded to each other to form a ring structure; and when $R^9$ and $R^{10}$ or $R^{11}$ are each an alkyl group or an alkenyl group, $R^9$ and $R^{10}$ or $R^{11}$ may be bonded to each other to form a ring structure).

The alkyl group and the alkenyl group may be linear, branched, or cyclic. In addition, the number of carbon atoms of the alkyl group is preferably 1 to 20, and more preferably 4 to 12. Moreover, the alkyl group may contain a hetero atom (preferably an oxygen atom), unless the effect of the present invention is impaired. The position of the C=C bond in the alkenyl group is not particularly limited, but may be at a terminal or internal position. Examples of the aryl group include phenyl group, methylphenyl group, benzyl group, and the like. The aryl group may contain a hetero atom (preferably an oxygen atom), unless the effect of the present invention is impaired. Examples of the alkyl group, the alkenyl group, and the aryl group containing a hetero atom include those having a functional group containing a hetero atom (preferably an oxygen atom), such as an ester group (preferably a carboxylic acid ester group (—O—C(=O)—R) or an alkyl ester group (—C(=O)—O—R)).

Moreover, $R^8$ and $R^{12}$ and/or $R^9$ and $R^{10}$ or $R^{11}$ may be bonded to each other to form a ring structure. Examples of such a ring structure include cyclic olefins such as cycloalkene and cycloalkadiene, and the like. In this case, a C=C bond may be present in a moiety other than the ring structure (for example, in any one of $R^9$ to $R^{11}$, when $R^8$ and $R^{12}$ are bonded to each other to form the ring structure).

Note, however, that the kinds and the numbers of carbon atoms of $R^8$ to $R^{12}$ in the formula (3) are determined depending on the kind of the internal olefin or the cyclic olefin represented by the formula (2) and on the position thereof to which the carboxyl group of the carboxylic acid is bonded. In addition, $R^{13}$ in the formula (3) is determined depending on the carboxylic acid.

For example, suppose a case where $R^4$ in the formula (2) is —$CR^{4a}R^{4b}R^{4c}$, and $R^7$ therein is —$CR^{7a}R^{7b}R^{7c}$, i.e., a case where the internal olefin or the cyclic olefin is a compound represented by the following formula (2a):

[Chem. 7]

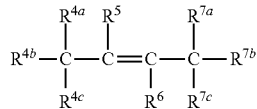
(2a)

(in the formula (2a), $R^5$ and $R^6$ are synonymous with $R^5$ and $R^6$ in the formula (2), respectively; $R^{4a}$ to $R^{4c}$ and $R^{7a}$ to $R^{7c}$ each independently represent one selected from the group consisting of a hydrogen atom, alkyl groups, alkenyl groups, and aryl groups; the alkyl group, the alkenyl group, and the aryl group may each contain a hetero atom (preferably, a functional group containing a hetero atom); when $R^6$ and any one of $R^{4a}$ to $R^{4c}$ are each an alkyl group or an alkenyl group, $R^6$ and the one of $R^{4a}$ to $R^{4c}$ may be bonded to each other to form a ring structure; and when $R^5$ and any one of $R^{7a}$ to $R^{7c}$ are each an alkyl group or an alkenyl group, $R^5$ and the one of $R^{7a}$ to $R^{7c}$ may be bonded to each other to form a ring structure). In such a case, a reaction of this compound with a carboxylic acid represented by the following formula (4):

 (4)

($R^{13}$ in the formula (4) is synonymous with $R^{13}$ in the formula (3))
results in the formation of the following α,β-unsaturated bond-containing ester compounds: the α,β-unsaturated bond-containing ester compounds formed by bonding a carboxyl group of the carboxylic acid to one of the carbon atoms constituting the C=C bond in the formula (2a), and represented by the following formulae (3a) and (3b):

[Chem. 8]

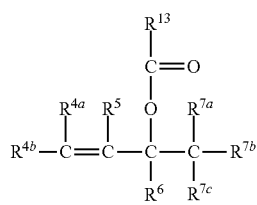
(3a)

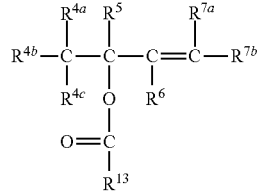
(3b)

(in the formulae (3a) and (3b), $R^{4a}$ to $R^{4c}$, $R^5$, $R^6$, and $R^{7a}$ to $R^{7c}$ are synonymous with $R^{4a}$ to $R^{4c}$, $R^5$, $R^6$, and $R^{7a}$ to $R^{7c}$ in the formula (2a), respectively; and $R^{13}$ is synonymous with $R^{13}$ in the formula (4)),
and/or α,β-unsaturated bond-containing ester compounds formed by bonding a carboxyl group of the carboxylic acid to one of the carbon atoms at the allylic positions in the formula (2a), and represented by the following formulae (3c) and (3d):

[Chem. 9]

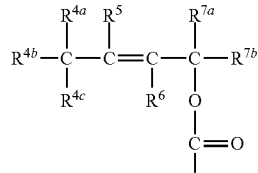
(3c)

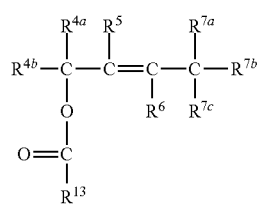
(3d)

(in the formulae (3c) to (3d), $R^{4a}$ to $R^{4c}$, $R^5$, $R^6$, and $R^{7a}$ to $R^{7c}$ are synonymous with $R^{4a}$ to $R^{4c}$, $R^5$, $R^6$, and $R^{7a}$ to $R^{7c}$ in the formula (2a), respectively; and $R^{13}$ is synonymous with $R^{13}$ in the formula (4)).

Note that, in the formula (3a), $R^{4a}$ and $R^{4b}$ correspond to $R^8$ and $R^9$ in the formula (3); $R^5$ corresponds to $R^{12}$ in the formula (3); and $R^6$ and —$CR^{7a}R^{7b}R^{7c}$ correspond to $R^{10}$ and $R^{11}$ in the formula (3). In addition, in the formula (3b), $R^{7a}$ and $R^{7b}$ correspond to $R^8$ and $R^9$ in the formula (3); $R^6$ corresponds to $R^{12}$ in the formula (3); and —$CR^{4a}R^{4b}R^{4c}$ and $R^5$ correspond to $R^{10}$ and $R^{11}$ in the formula (3).

Moreover, in the formula (3c), —$CR^{4a}R^{4b}R^{4c}$ and $R^5$ correspond to $R^8$ and $R^9$ in the formula (3); $R^6$ corresponds to $R^{12}$ in the formula (3); and $R^{7a}$ and $R^{7b}$ correspond to $R^{10}$ and $R^{11}$ in the formula (3). In addition, in the formula (3d), —$CR^{7a}R^{7b}R^{7c}$ and $R^6$ correspond to $R^8$ and $R^9$ in the formula (3); $R^5$ corresponds to $R^{12}$ in the formula (3); and $R^{4a}$ and $R^{4b}$ correspond to $R^{10}$ and $R^{11}$ in the formula (3).

Moreover, after an α,β-unsaturated bond-containing monoester compound is formed by the esterification reaction of the olefin through oxidative bonding of a carboxyl group as described above, the esterification reaction through oxidative bonding of a carboxyl group is allowed to further proceed. In such a case, the α,β-unsaturated bond-containing monoester compound reacts with the carboxylic acid, so that a carboxyl group of the carboxylic acid is bonded to at least one of carbon atoms constituting the C=C bond in the α,β-unsaturated bond-containing monoester compound and carbon atoms at allylic positions therein, to form an α,β-unsaturated bond-containing diester compound.

In the present invention, the mode of the esterification reaction of the olefin through oxidative bonding of a carboxyl group is not particularly limited, as long as the palladium catalyst and the internal olefin or the cyclic olefin can be brought into contact with each other. For example, the esterification reaction can be carried out in any form of gas-liquid reaction and/or liquid-liquid reaction according to the kinds of the internal olefin or the cyclic olefin and the palladium catalyst used. Moreover, a batch, semi-batch, semi-continuous, or continuous-flow reaction system, or a combination thereof can be employed. In addition, the method for feeding each component is not particularly limited, but the component may be fed in a form of liquid or a form of gas.

Specific examples of the production process include a batch method in which the oxygen-containing gas and a catalyst solution prepared by mixing the palladium catalyst with the amide-based solvent or a mixture solution obtained by mixing the internal olefin or the cyclic olefin with the catalyst solution are charged in a batch reactor, and allowed to react with each other; a semi-batch method or a semi-continuous method in which the internal olefin or the cyclic olefin and the oxygen-containing gas are continuously fed into the catalyst solution, or the oxygen-containing gas is continuously fed into the mixture solution; a continuous-flow method in which the catalyst solution, the internal olefin or the cyclic olefin, and the oxygen-containing gas are caused to flow simultaneously through a reaction region; and the like.

In the present invention, when the internal olefin or the cyclic olefin and the oxygen-containing gas are continuously fed into the catalyst solution, the feed rate of the internal olefin or the cyclic olefin is preferably 10 to 5000 mol/h per mole of palladium. If the feed rate of the internal olefin or the cyclic olefin is lower than the lower limit, the amount of the α,β-unsaturated bond-containing ester compound manufactured per unit time tends to decrease. Meanwhile, if the feed rate exceeds the upper limit, the α,β-unsaturated bond-containing ester compound tends not to be obtained at a high yield because of the formation of Pd Black, which is an inactive species. Note that the feed rate of the oxygen-containing gas is adjusted as appropriate, such that the oxygen pressure inside the reaction system can be within the above-described range.

In the present invention, the reaction temperature for carrying out the esterification reaction through oxidative bonding of a carboxyl group is preferably 0 to 200° C., and more preferably 20 to 100° C. If the reaction temperature is lower than the lower limit, the reaction rate is decelerated. Meanwhile, if the reaction temperature exceeds the upper limit, a side reaction such as isomerization of the olefin occurs. In either case, the yield of the α,β-unsaturated bond-containing ester compound tends to decrease.

Moreover, in the present invention, a concentration of a copper catalyst, which is used in the conventional Wacker process, is preferably 0.03 mol/L or less, more preferably 0.01 mol/L or less, and particularly preferably 0.003 mol/L or less. If the concentration of the copper catalyst exceeds the upper limit, the yield of the α,β-unsaturated bond-containing ester compound tends to decrease. From such a viewpoint, it is most preferable in the present invention to esterify the internal olefin or the cyclic olefin through oxidative bonding of a carboxyl group in the absence of any copper catalyst. In the conventional Wacker process, the copper catalyst accelerates the reoxidation of the palladium catalyst. On the other hand, in an esterification reaction of the internal olefin or the cyclic olefin through oxidative bonding of a carboxyl group, such as the reaction of the present invention, the yield of the α,β-unsaturated bond-containing ester compound tends to decrease if a copper catalyst is coexistent. Accordingly, the copper catalyst presumably inhibits an activation of the palladium catalyst which is supposed to proceed efficiently with molecular oxygen.

The α,β-unsaturated bond-containing ester compound thus obtained can be obtained as any one of a single compound and a mixture, which have a desired purity or composition, by separation and purification in a usual manner. Since a side reaction hardly occurs during the esterification reaction of the olefin through oxidative bonding of a carboxyl group in the production process of the present invention, the unreacted raw material can be recovered and reused for the production of the α,β-unsaturated bond-containing ester compound. The amide-based solvent and the palladium catalyst can also be separated and recovered, and then used repeatedly. At this time, the palladium catalyst can be regenerated, if necessary.

EXAMPLES

Hereinafter, the present invention will be described more specifically on the basis of Examples and Comparative Example. However, the present invention is not limited to Examples below.

Example 1

Palladium chloride (62 mg, 0.35 mmol), sodium acetate (410 mg, 5 mmol), acetic acid (3.1 g (3 ml), 50 mmol), and dimethylacetamide (DMA, 5 ml) were charged in a pressure vessel. The pressure inside the vessel was reduced, and 2-butene (450 mg, 8 mmol) was added thereto. Then, the pressure inside the vessel was raised to 0.6 MPa by feeding oxygen gas thereto, and an esterification reaction was conducted at 80° C. for 4 hours.

After completion of the reaction, the product was analyzed by using a gas chromatograph equipped with an FID detector ("GC-2014" manufactured by Shimadzu Corporation, column: KOCL 3 m). As a result, it was found that an acetoxyl group (AcO—) was bonded to a carbon atom in the C=C bond of 2-butene or a carbon atom at an allylic position thereof, so that 2-butene-1-acetate and 3-butene-2-acetate were formed. Accordingly, 2-butene was presumably esterified by oxidatively bonding a carboxyl group as shown in the following reaction formula (I):

[Chem. 10]

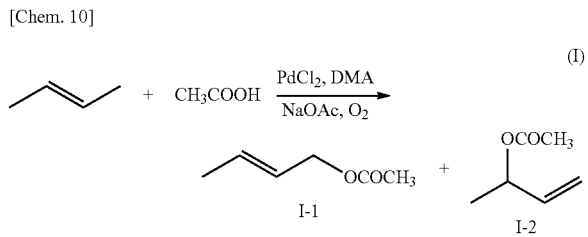

In addition, Table 1 shows the conversion of 2-butene, the total yield of 2-butene-1-acetate and 3-butene-2-acetate based on the amount of 2-butene charged, and the isomer ratio between 2-butene-1-acetate and 3-butene-2-acetate.

Example 2

An esterification reaction was conducted in the same manner as in Example 1, except that trans-3-hexene (84 mg, 1.0 mmol) was used instead of 2-butene, the amount of palladium chloride was changed to 8.8 mg (0.05 mmol), the amount of sodium acetate was changed to 16.4 mg (0.2 mmol), the amount of acetic acid was changed to 0.2 g (0.2 ml, 3.3 mmol), molecular sieves (0.2 g) having a pore size of 3 Å were added, and the reaction time was changed to 24 hours.

The product was analyzed in the same manner as in Example 1. As a result, it was found that an acetoxyl group (AcO—) was bonded to a carbon atom in the C═C bond of trans-3-hexene or a carbon atom at an allylic position thereof, so that 3-hexene-2-acetate and 4-hexene-3-acetate were formed. Accordingly, trans-3-hexene was presumably esterified by oxidatively bonding a carboxyl group as shown in the following reaction formula (II):

[Chem. 11]

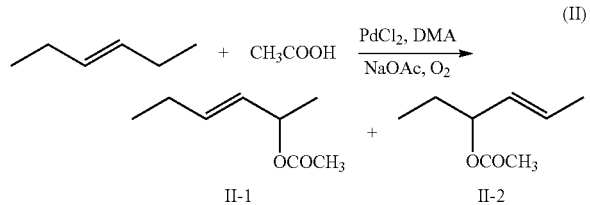

In addition, Table 1 shows the conversion of trans-3-hexene and the total yield of 3-hexene-2-acetate and 4-hexene-3-acetate based on the amount of trans-3-hexene charged.

Example 3

An esterification reaction was conducted in the same manner as in Example 2, except that the reaction time was changed to 40 hours. The product was analyzed in the same manner as in Example 2 to determine the conversion of trans-3-hexene and the total yield of 3-hexene-2-acetate and 4-hexene-3-acetate based on the amount of trans-3-hexene charged. Table 1 shows the results thereof.

Example 4

An esterification reaction was conducted in the same manner as in Example 3, except that the pressure inside the vessel was raised to 0.1 MPa by feeding oxygen gas. The product was analyzed in the same manner as in Example 2 to determine the conversion of trans-3-hexene and the total yield of 3-hexene-2-acetate and 4-hexene-3-acetate based on the amount of trans-3-hexene charged. Table 1 shows the results thereof.

Example 5

An esterification reaction was conducted in the same manner as in Example 3, except that the amount of trans-3-hexene was changed to 42 mg (0.5 mmol). The product was analyzed in the same manner as in Example 2 to determine the conversion of trans-3-hexene and the total yield of 3-hexene-2-acetate and 4-hexene-3-acetate based on the amount of trans-3-hexene charged. Table 1 shows the results thereof.

Example 6

An esterification reaction was conducted in the same manner as in Example 2, except that trans-4-octene (112 mg, 1.0 mmol) was used instead of 2-butene, and the amount of palladium chloride was changed to 17.7 mg (0.1 mmol).

The product was analyzed in the same manner as in Example 1. As a result, it was found that an acetoxyl group (AcO—) was bonded to a carbon atom in the C═C bond of trans-4-octene or a carbon atom at an allylic position thereof, so that 4-octene-3-acetate and 5-octene-4-acetate were formed. Accordingly, trans-4-octene was presumably esterified by oxidatively bonding a carboxyl group as shown in the following reaction formula (III):

[Chem. 12]

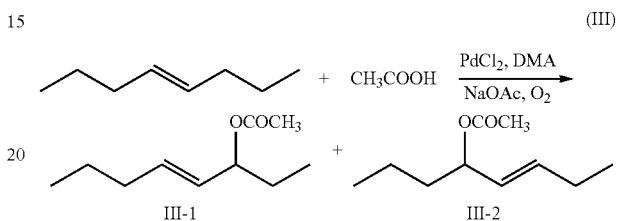

In addition, Table 1 shows the conversion of trans-4-octene and the total yield of 4-octene-3-acetate and 5-octene-4-acetate based on the amount of trans-4-octene charged.

Example 7

An esterification reaction was conducted in the same manner as in Example 6, except that the reaction time was changed to 40 hours. The product was analyzed in the same manner as in Example 6 to determine the conversion of trans-4-octene and the total yield of 4-octene-3-acetate and 5-octene-4-acetate based on the amount of trans-4-octene charged. Table 1 shows the results thereof.

Example 8

An esterification reaction was conducted in the same manner as in Example 1, except that cyclohexene (504 mg, 6.15 mmol) was used instead of 2-butene, the amount of palladium chloride was changed to 55 mg (0.31 mmol), the amount of sodium acetate was changed to 902 mg (11 mmol), and the amount of acetic acid was changed to 1.2 g (1.2 ml, 19.8 mmol).

The product was analyzed in the same manner as in Example 1. As a result, it was found that a product (2-cyclohexene-1-acetate) in which an acetoxyl group (AcO—) was bonded was formed. Accordingly, cyclohexene was presumably esterified by oxidatively bonding a carboxyl group as shown in the following reaction formula (IV):

[Chem. 13]

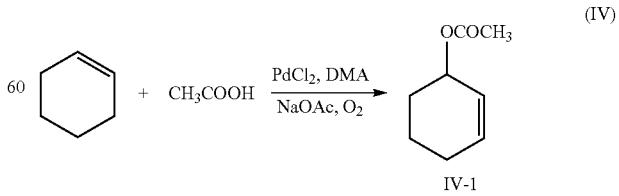

In addition, Table 1 shows the conversion of cyclohexene and the yield of 2-cyclohexene-1-acetate.

Comparative Example 1

An esterification reaction was conducted in the same manner as in Example 1, except that sodium acetate was not used. The product was analyzed in the same manner as in Example 1. However, the formation of 2-butene-1-acetate or the formation of 3-butene-2-acetate was not detected, and 2-butene, which was a raw material, was recovered as it was.

TABLE 1

| | Olefin (amount of charge) | Catalyst system | Reaction time (hour) | Oxygen gas (MPa) | Acetate | Conversion (%) | Yield of acetate (%) | Isomer ratio (%) |
|---|---|---|---|---|---|---|---|---|
| Ex. 1 | 2-butene (8 mmol) | PdCl$_2$/DMA | 4 | 0.6 | 2-buten-1-acetate (Formula I-1) 3-buten-2-acetate (Formula I-2) | 71 | 71 | 52 48 |
| Ex. 2 | trans-3-hexene (1 mmol) | PdCl$_2$/DMA | 24 | 0.6 | 3-hexene-2-acetate (Formula II-1) 4-hexene-3-acetate (Formula II-2) | 71 | 31 | — — |
| Ex. 3 | trans-3-hexene (1 mmol) | PdCl$_2$/DMA | 40 | 0.6 | 3-hexene-2-acetate (Formula II-1) 4-hexene-3-acetate (Formula II-2) | 89 | 44 | — — |
| Ex. 4 | trans-3-hexene (1 mmol) | PdCl$_2$/DMA | 40 | 0.1 | 3-hexene-2-acetate (Formula II-1) 4-hexene-3-acetate (Formula II-2) | 83 | 23 | — — |
| Ex. 5 | trans-3-hexene (0.5 mmol) | PdCl$_2$/DMA | 40 | 0.6 | 3-hexene-2-acetate (Formula II-1) 4-hexene-3-acetate (Formula II-2) | 95 | 30 | — — |
| Ex. 6 | trans-4-octene (1 mmol) | PdCl$_2$/DMA | 24 | 0.6 | 4-octene-3-acetate (Formula III-1) 5-octene-4-acetate (Formula III-2) | 69 | 36 | — — |
| Ex. 7 | trans-4-octene (1 mmol) | PdCl$_2$/DMA | 40 | 0.6 | 4-octene-3-acetate (Formula III-1) 5-octene-4-acetate (Formula III-2) | 77 | 43 | — — |
| Ex. 8 | cyclohexene (6.15 mmol) | PdCl$_2$/DMA | 4 | 0.6 | 2-cyclohexene-1-acetate (Formula IV-1) | 9 | 6.5 | — |
| Comp. Ex. 1 | 2-butene (8 mmol) | PdCl$_2$/DMA | 4 | 0.6 | 2-buten-1-acetate (Formula I-1) 3-buten-2-acetate (Formula I-2) | 0 | 0 | 0 0 |

As is apparent from the results shown in Table 1, in the cases (Examples 1 to 8) where the internal olefins were reacted with acetic acid in DMA in the presence of the PdCl$_2$ catalyst and sodium acetate, it was found that an acetoxyl group was successfully bonded to a carbon atom in the C═C bond of the internal olefins or a carbon atom at an allylic position thereof, so that it was possible to conduct esterification of the internal olefin through oxidative bonding of a carboxyl group. In particular, it was found that 2-butene-1-acetate and 3-butene-2-acetate were successfully manufactured at a high yield in the case (Example 1) where 2-butene was used as the internal olefin. On the other hand, it was difficult to esterify the internal olefin through oxidative bonding of a carboxyl group in the case (Comparative Example 1) where sodium acetate was not used.

Example 9

An esterification reaction through oxidative bonding of a carboxyl group was conducted in the same manner as in Example 1, except that 2-butene-1-acetate (354 mg, 3.1 mmol) obtained in Example 1 was used instead of 2-butene, the amount of palladium chloride was changed to 28.3 mg (0.16 mmol), the amount of sodium acetate was changed to 48.4 mg (0.59 mmol), the amount of acetic acid was changed to 0.63 g (0.6 ml, 10.5 mmol), and the amount of dimethylacetamide (DMA) was changed to 15 ml.

The product was analyzed in the same manner as in Example 1. As a result, it was found that an acetoxyl group (AcO—) was bonded to a carbon atom in the C═C bond of 2-butene-1-acetate or a carbon atom at an allylic position thereof, so that 2-butene-1,1-diacetate, 3-butene-1,2-diacetate, 1-butene-1,3-diacetate, 2-butene-1,3-diacetate, and 2-butene-1,4-diacetate were formed. Accordingly, 2-butene-1-acetate was presumably esterified by oxidatively bonding a carboxyl group as shown in the following reaction formula (V):

[Chem. 14]

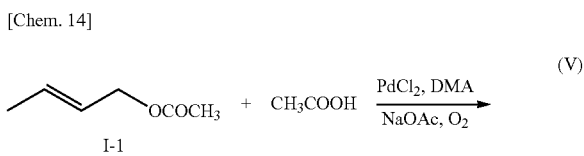

(V)

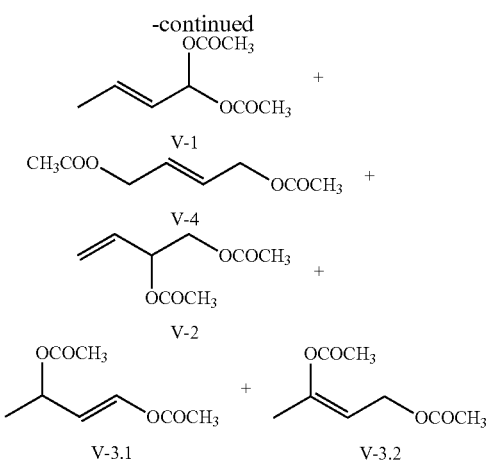

In addition, Table 2 shows the conversion of 2-butene-1-acetate, the overall selectivity for the diacetates, and the isomer ratio between the diacetates.

Example 10

An esterification reaction through oxidative bonding of a carboxyl group was conducted in the same manner as in Example 1, except that methyl oleate (916.5 mg, 3.1 mmol) was used instead of 2-butene, the amount of palladium chloride was changed to 28.3 mg (0.16 mmol), the amount of sodium acetate was changed to 48.4 mg (0.59 mmol), the amount of acetic acid was changed to 0.63 g (0.6 ml, 10.5 mmol), and the amount of dimethylacetamide (DMA) was changed to 15 ml.

The product was analyzed in the same manner as in Example 1. As a result, it was found that an acetoxyl group (AcO—) was bonded to a carbon atom in the C═C bond of methyl oleate or a carbon atom at an allylic position thereof, so that methyl oleate-8-acetate and methyl oleate-11-acetate were formed. Accordingly, methyl oleate was presumably esterified by oxidatively bonding a carboxyl group as shown in the following reaction formula (VI):

[Chem. 15]

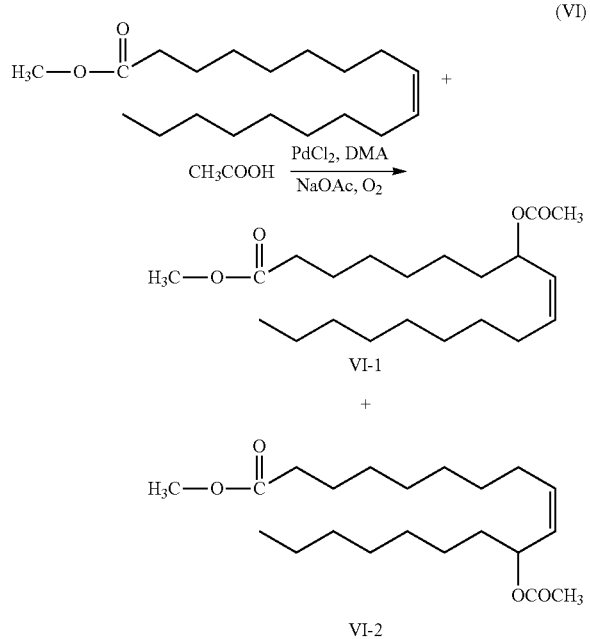

In addition, the conversion of methyl oleate and the overall selectivity for methyl oleate-8-acetate and methyl oleate-11-acetate were determined. Table 2 shows the results thereof.

TABLE 2

| | Olefin (amount of charge) | Catalyst system | Reaction time (hour) | Oxygen gas (MPa) | Acetate | Conversion (%) | Selectivity for acetates (%) | Isomer ratio (%) |
|---|---|---|---|---|---|---|---|---|
| Ex. 9 | 2-buten-1-acetate (3.1 mmol) | PdCl$_2$/DMA | 4 | 0.6 | 2-buten-1,1-diacetate (Formula V-1) | 63.5 | 47.9 | 17.5 |
| | | | | | 3-buten-1,2-diacetate (Formula V-2) | | | 47.0 |
| | | | | | 1-buten-1,3-diacetate (Formula V-3.1) | | | 27.1 |
| | | | | | 2-buten-1,3-diacetate (Formula V-3.2) | | | |
| | | | | | 2-buten-1,4-diacetate (Formula V-4) | | | 8.4 |
| Ex. 10 | methyl oleate (3.1 mmol) | PdCl$_2$/DMA | 4 | 0.6 | methyl oleate-8-acetate | 19.5 | 82.6 | — |
| | | | | | methyl oleate-11-acetate | | | — |

As is apparent from the results shown in Table 2, also in the cases (Examples 9 and 10) where the internal olefins having a functional group containing a hetero atom was reacted with acetic acid in DMA in the presence of the PdCl$_2$ catalyst and sodium acetate, it was found that an acetoxyl group was successfully bonded to a carbon atom in the C=C bond of the internal olefins or a carbon atom at an allylic position thereof, without oxidation of the functional group containing a hetero atom, so that it was possible to conduct esterification of the internal olefin through oxidative bonding of a carboxyl group.

INDUSTRIAL APPLICABILITY

As described above, according to the present invention, an α,β-unsaturated bond-containing ester compound, which is difficult to manufacture by conventional methods from an internal olefin or a cyclic olefin, can be manufactured therefrom at a relatively high yield.

Accordingly, when α,β-unsaturated bond-containing ester compounds are manufactured by using, as a raw material, a mixture olefin containing not only a terminal olefin, but also an internal olefin or a cyclic olefin, the process for producing an α,β-unsaturated bond-containing ester compound of the present invention makes it possible to manufacture an α,β-unsaturated bond-containing ester compound not only from the terminal olefin, but also from the internal olefin or the cyclic olefin. Hence, the process is an industrially excellent process for producing an α,β-unsaturated bond-containing ester compound, because this process makes it possible to effectively use internal olefins and cyclic olefins, which have to be removed as unreacted substances in conventional methods for manufacturing an α,β-unsaturated bond-containing ester compound.

In particular, the process for producing an α,β-unsaturated bond-containing ester compound of the present invention makes it possible to obtain not only an α,β-unsaturated bond-containing monoester compound, but also an α,β-unsaturated bond-containing diester compound by causing the reaction to proceed further.

Accordingly, the process for producing an α,β-unsaturated bond-containing ester compound of the present invention is useful as a process for producing an α,β-unsaturated bond-containing diester compound, which is a raw material of diols such as 1,2-butanediol, 1,3-butanediol, and 1,4-butanediol.

The invention claimed is:

1. A process for producing an unsaturated bond-containing ester compound, comprising:

reacting an internal olefin or a cyclic olefin having one carbon-carbon double bond or more at a position other than terminals of a molecule thereof (the internal olefin and the cyclic olefin may each contain a hetero atom) with a carboxylic acid having a carboxylic group in an amide-based solvent in the presence of a palladium catalyst, a base, and molecular oxygen, to thereby obtain an ester compound having an unsaturated bond, wherein the amide-based solvent is represented by the following formula (1):

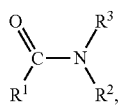

wherein the formula (1), R$^1$ represents an alkyl group having 1 to 4 carbon atoms; R$^2$ and R$^3$ each independently represent an alkyl group having 1 to 4 carbon atoms or an aryl group;

and when $R^1$ and $R^2$ are alkyl groups, $R^1$ and $R^2$ may be bonded to each other to form a ring structure;

the internal olefin or the cyclic olefin is a compound represented by the following formula (2):

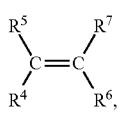

(2)

wherein the formula (2), $R^4$ to $R^7$ each independently represent one selected from the group consisting of a hydrogen atom, alkyl groups, alkenyl groups, and aryl groups; the alkyl group, the alkenyl group, and the aryl group may each contain a hetero atom, at least one of $R^4$ and $R^5$ is any one of alkyl groups, alkenyl groups, and aryl groups, at least one of $R^6$ and $R^7$ is any one of alkyl groups, alkenyl groups, and aryl groups; when $R^4$ and $R^6$ are each an alkyl group or an alkenyl group, $R^4$ and $R^6$ may be bonded to each other to form a ring structure, and when $R^5$ and $R^7$ are each an alkyl group or an alkenyl group, $R^5$ and $R^7$ may be bonded to each other to form a ring structure;

the ester compound is represented by the following formula (3):

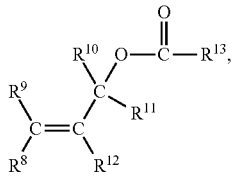

(3)

wherein the formula (3), $R^8$ to $R^{13}$ each independently represent one selected from the group consisting of a hydrogen atom, alkyl groups, alkenyl groups, and aryl groups; the alkyl group, the alkenyl group, and the aryl group may each contain a hetero atom; at least one of $R^8$ to $R^{11}$ is any one of alkyl groups, alkenyl groups, and aryl groups; when $R^8$ and $R^{12}$ are each an alkyl group or an alkenyl group, $R^8$ and $R^{12}$ may be bonded to each other to form a ring structure; and when $R^9$ and $R^{10}$ or $R^{11}$ are each an alkyl group or an alkenyl group, $R^9$ and $R^{10}$ or $R^{11}$ may be bonded to each other to form a ring structure;

the palladium catalyst is a palladium halide; and the ester compound is formed by bonding an oxygen atom in the carboxyl group of the carboxylic acid to at least one of carbon atoms constituting the carbon-carbon double bond and carbon atoms at allylic positions of the internal olefin or the cyclic olefin.

2. The process for producing an unsaturated bond-containing ester compound according to claim 1, wherein the carboxylic acid is acetic acid, and an acetoxyl group is bonded to a carbon atom at an allylic position of the ester compound having an unsaturated bond.

3. The process for producing an unsaturated bond-containing ester compound according to claim 1, wherein the internal olefin or the cyclic olefin does not have any carbon-carbon double bond at the terminals of the molecule thereof.

4. The process for producing an unsaturated bond-containing ester compound according to claim 1, wherein the amide-based solvent is N,N-dimethylacetamide.

5. The process for producing an unsaturated bond-containing ester compound according to claim 1, wherein the internal olefin or the cyclic olefin is reacted with the carboxylic acid in the absence of any copper catalyst.

6. The process for producing an unsaturated bond-containing ester compound according to claim 1, wherein the concentration of the palladium catalyst is 0.002 to 1 mol/L.

7. A process for producing an unsaturated bond-containing diester compound, comprising:

reacting an unsaturated bond-containing monoester compound obtained by the process for producing an unsaturated bond-containing ester compound according to claim 1 with a carboxylic acid having a carboxylic group in an amide-based solvent in the presence of a palladium catalyst, a base, and molecular oxygen, to thereby obtain a diester compound having an unsaturated bond, wherein the amide-based solvent is represented by the following formula (1):

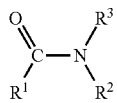

(1)

wherein the formula (1), $R^1$ represents an alkyl group having 1 to 4 carbon atoms; $R^2$ and $R^3$ each independently represent an alkyl group having 1 to 4 carbon atoms or an aryl group; and when $R^1$ and $R^2$ are alkyl groups, $R^1$ and $R^2$ may be bonded to each other to form a ring structure, the palladium catalyst is a palladium halide, and the diester compound is formed by bonding an oxygen atom in the carboxyl group of the carboxylic acid to at least one of carbon atoms constituting a carbon-carbon double bond in the unsaturated bond-containing monoester compound and carbon atoms at allylic positions of the unsaturated bond-containing monoester compound.

\* \* \* \* \*